United States Patent
Dreher et al.

(10) Patent No.: US 9,993,782 B2
(45) Date of Patent: Jun. 12, 2018

(54) STIRRER INSTALLATION AID AND METHOD FOR INSTALLING A STIRRER ELEMENT IN A BIOREACTOR

(71) Applicant: Sartorius Stedim Biotech GmbH, Goettingen (DE)

(72) Inventors: Thomas Dreher, Goettingen (DE); Oliver Scheibe, Stadthagen (DE); Gerhard Greller, Goettingen (DE); Ute Husemann, Goettingen (DE); Oscar-Werner Reif, Hannover (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 443 days.

(21) Appl. No.: 14/432,616

(22) PCT Filed: Aug. 29, 2013

(86) PCT No.: PCT/EP2013/067928
§ 371 (c)(1),
(2) Date: Mar. 31, 2015

(87) PCT Pub. No.: WO2014/053276
PCT Pub. Date: Apr. 10, 2014

(65) Prior Publication Data
US 2015/0273416 A1    Oct. 1, 2015

(30) Foreign Application Priority Data
Oct. 1, 2012  (DE) .................. 10 2012 019 215

(51) Int. Cl.
*B01F 15/00*   (2006.01)
*B01F 7/00*    (2006.01)
*C12M 1/06*    (2006.01)

(52) U.S. Cl.
CPC .......... *B01F 15/00* (2013.01); *B01F 7/00008* (2013.01); *B01F 15/00922* (2013.01); *C12M 27/02* (2013.01); *Y10T 29/49316* (2015.01)

(58) Field of Classification Search
CPC    B01F 15/00; B01F 15/00922; B01F 7/00008; C12M 27/02; Y10T 29/49316
See application file for complete search history.

(56) References Cited

U.S. PATENT DOCUMENTS 2,859,019 A   11/1958   O'Neil, Jr.
6,110,731 A   8/2000    Murofushi et al.
(Continued)

FOREIGN PATENT DOCUMENTS

DE   561 724     10/1932
DE   2 061 882   6/1972
(Continued)

OTHER PUBLICATIONS

International Search Report dated Nov. 7, 2013.

*Primary Examiner* — Nathan A Bowers
*Assistant Examiner* — Lydia Edwards
(74) *Attorney, Agent, or Firm* — Gerald E. Hespos; Michael J. Porco; Matthew T. Hespos

(57) ABSTRACT

A bioreactor has a stirrer shaft that is driveable by a drive and on which a stirrer element is positioned. The position of the stirrer element is determined by a stirrer installation aid. The stirrer installation aid has a free end with an abutment surface on which the free end of the stirrer element abuts. The stirrer installation aid is designed as a sleeve that comprises a slot extending between the axial ends of the sleeve. The slot is delimited by opposite flanks of a wall, and the sleeve is placed on the stirrer shaft. The stirrer installation aid can be pulled off laterally from the stirrer shaft. A
(Continued)

method for installing the stirrer element on the stirrer shaft arranged in the bioreactor also is provided.

6 Claims, 5 Drawing Sheets

(56) References Cited

U.S. PATENT DOCUMENTS

| | | |
|---|---|---|
| 2009/0275121 A1 | 11/2009 | Greller et al. |
| 2011/0026360 A1 | 2/2011 | Greller et al. |

FOREIGN PATENT DOCUMENTS

| | | |
|---|---|---|
| DE | 42 32 935 | 4/1994 |
| DE | 20 2007 005 868 | 8/2007 |
| DE | 10 2006 021 984 | 11/2007 |
| DE | 10 2007 007 827 | 11/2008 |
| DE | 10 2009 018 209 | 10/2009 |
| EP | 1 577 376 | 9/2005 |
| EP | 2 024 072 | 10/2009 |
| EP | 2 274 085 | 9/2012 |

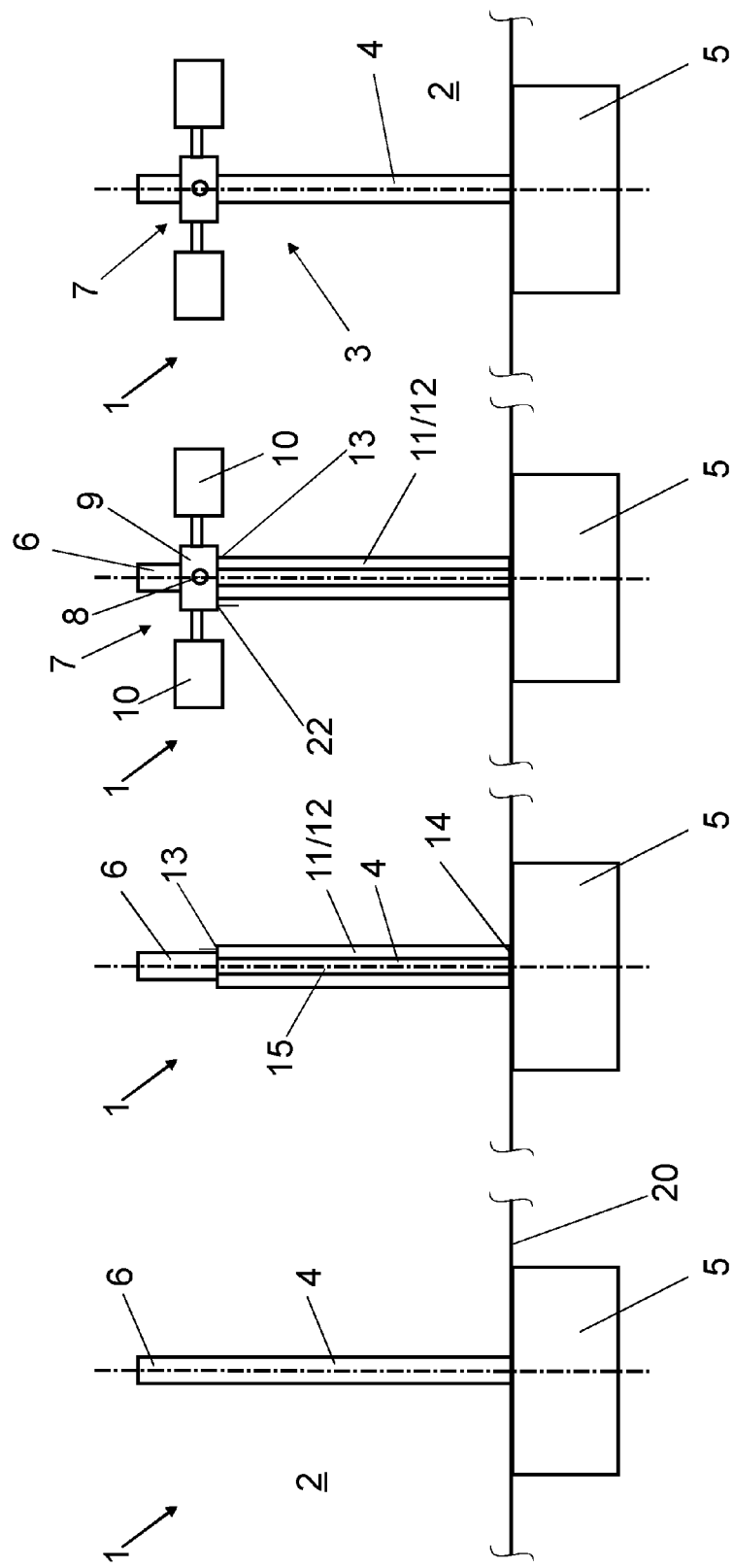

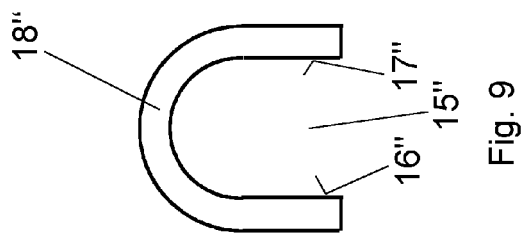
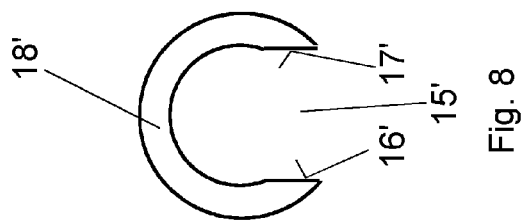
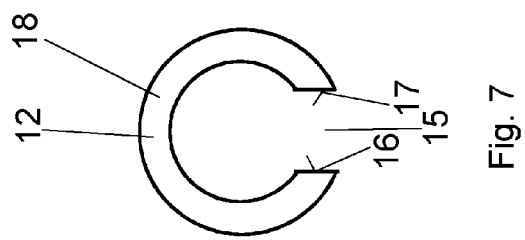
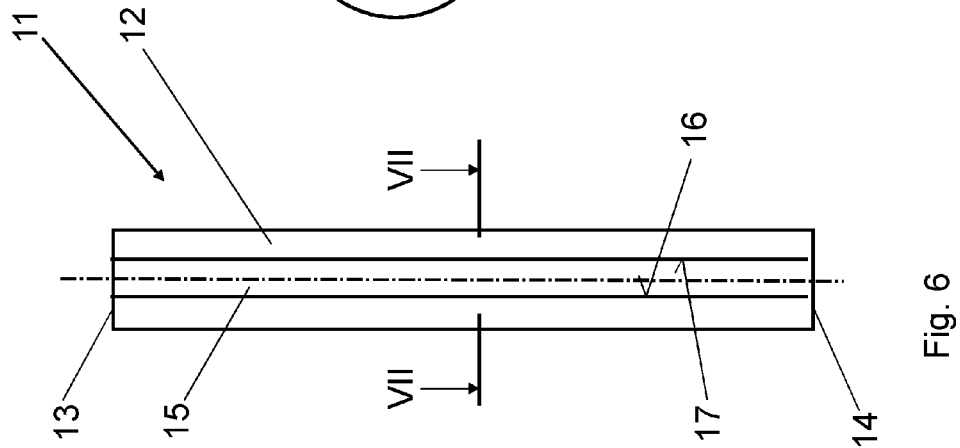

STIRRER INSTALLATION AID AND METHOD FOR INSTALLING A STIRRER ELEMENT IN A BIOREACTOR

BACKGROUND

1. Field of the Invention

The invention relates to the use of a sleeve which comprises a slot extending between the axial ends of the sleeve and delimited by opposite flanks of the wall, as a stirrer installation aid.

The invention further relates to a method to install a stirrer element on a stirrer shaft arranged within a bioreactor.

The invention further relates to a bioreactor with a stirrer shaft on which a stirrer element is positionable, the shaft being driveable by a drive.

2. Description of the Related Art

When commissioning bioreactors that have a stirrer, it is necessary to mount stirrer elements on the stirrer shaft of the stirrer. To ensure optimal flow characteristics, care must be taken that the stirrer elements are placed at a defined position on the stirrer shaft. Installation and adjustment of the height, i.e. in particular the spacing between the stirrer element and the reactor floor and/or ceiling, is often a complicated and time-consuming step.

With regard to reusable bioreactors in particular, the stirrer elements must always be removed during cleaning and then reinstalled on the stirrer shaft. This is difficult since the spacing must be measured and at the same time the stirrer element must be screwed in place. Moreover, in many cases the installation space is relatively difficult to access and the process of determining and maintaining the length during installation is also difficult.

A sleeve/clamping sleeve is known from DE 20 2007 007 827 U1 that is expandable and has a slot extending between its axial ends, said slot being delimited by the opposite flanks of the wall. The known sleeve is used in combination with clamp fittings for pipes.

The problem of the present invention is to simplify positioning of stirrer elements on stirrer shafts and to improve the precision of their positioning.

SUMMARY OF THE INVENTION

The problem of the present invention is solved by a sleeve that comprises a slot extending between the axial ends of the sleeve and delimited by opposite flanks of a wall of the sleeve, as a removable stirrer installation aid for positioning a stirrer element on a stirrer shaft of a bioreactor.

The stirrer installation aid designed as a sleeve with a slot along its length enables the sleeve simply to be used as a type of spacer that can be easily pulled off laterally from the stirrer shaft after the stirrer element has been positioned and fixed in place. This significantly improves the precision of positioning while at the same time considerably simplifying the positioning or installing of the stirrer element on the stirrer shaft.

The stirrer installation aid may be placed on the stirrer shaft, so that its first axial end abuts on the mounting of the stirrer shaft, and the stirrer element then abuts on the free, second axial end of the stirrer installation aid placed on the stirrer shaft. The stirrer element then is fastened to the stirrer shaft, and installation aid is laterally pulled off. The stirrer installation aid can then be reused in another installation process. The stirrer installation aid is fastened in such a way that the stirrer installation aid abuts on the end facing the drive for the stirrer element (e.g. a motor). For example, this end can be the reactor floor or an abutment surface of a mounting or guide flange.

The stirrer installation aid can be made of an elastic material and be expandable. The elastic material allows the stirrer installation aid to exert a clamping action when placed on the stirrer shaft and to maintain its position, which facilitates handling of the stirrer installation aid. The expandable nature of the sleeve also makes it easy to remove afterwards.

The stirrer installation aid is C-shaped in cross section. It is fundamentally also possible, however, to design the stirrer installation aid with a "U"-shaped cross section.

The sleeve length is determined by the distance between the axial ends and it in turn determines the position of the stirrer element on the stirrer shaft.

A method to install a stirrer element on a stirrer shaft arranged within a bioreactor may comprise the following steps:

a) placing on the stirrer shaft, a sleeve which is slotted in the axial longitudinal direction over the entire length of the sleeve, which sleeve forms a stirrer installation aid, b) placing the stirrer element on the free end of the stirrer shaft until it abuts on the adjacent end of the sleeve, c) fixing the stirrer element on the stirrer shaft, and d) removing the stirrer installation aid.

Placing the sleeve with a longitudinal slot, which forms the stirrer installation aid, on the stirrer shaft makes it possible to easily and reliably place the stirrer element in its predetermined position and fasten it to the stirrer shaft by placing the stirrer element on the free end of the stirrer shaft until it abuts on the adjacent end of the sleeve. When no longer required, the stirrer installation aid can then be easily removed. Its longitudinal slot allows the stirrer installation aid to be easily pulled off laterally from the stirrer shaft.

The method according to the invention may install multiple stirrer elements on a stirrer shaft arranged within a bioreactor, so that at least one additional stirrer element is installed on the stirrer shaft arranged within the bioreactor after installation of a first stirrer element, wherein the following steps are carried out:

a') placing a second sleeve which is slotted in the axial longitudinal direction over the entire length of the sleeve, which sleeve forms a stirrer installation aid, on the first stirrer element fixed to the stirrer shaft, b') placing a second stirrer element on the free end of the stirrer shaft until it abuts on the adjacent end of the second sleeve, c') fixing the second stirrer element on the stirrer shaft, d') removing the second sleeve, and e') if needed, repeating steps a') to d') in order to fix additional stirrer elements on the stirrer shaft.

The advantage of this embodiment is that multiple stirrer elements can be fixed equidistantly on the stirrer shaft quickly, efficiently and at precisely reproducible spacings if sleeves of the same length are used in each of steps a') to d') and possibly e'). In this variation, the same sleeve that was used to install the previous stirrer elements can be used as the second and additional sleeves. On the other hand, various, structurally identical sleeves can be used to install multiple stirrer elements. Alternatively, stirrer elements can be fixed at different distances along the stirrer shaft quickly, efficiently and at precisely reproducible spacings if sleeves of different lengths are used in each of steps a') to d') and possibly e').

The invention also relates to a bioreactor where the position of the stirrer element is determined by a stirrer installation aid, on the free end of which the stirrer element abuts by means of an abutment surface, and in that the stirrer installation aid is designed as a sleeve which comprises a slot extending between the axial ends of the sleeve, said slot being delimited by opposite flanks of the wall, and said sleeve can be placed on the stirrer shaft, and in that the stirrer installation aid can be pulled off laterally from the stirrer shaft.

The bioreactor therefore has the advantages described above.

Further features and advantages of the invention result from the following specific description and the drawings.

BRIEF DESCRIPTION OF THE DRAWINGS

FIG. 2 is a lateral detail view of a bioreactor with a stirrer shaft.

FIG. 3 is a lateral detail view of the bioreactor from FIG. 2 with a stirrer installation aid.

FIG. 4 is a lateral detail view of the bioreactor from FIG. 3 with a stirrer element in place.

FIG. 5 is a lateral detail view of the bioreactor from FIG. 4 from which the stirrer installation aid has been removed.

FIG. 6 is a lateral view of a stirrer installation aid.

FIG. 7 is a cross section of the stirrer installation aid from FIG. 6, cut along Line VII-VII.

FIG. 8 is an additional cross section of a stirrer installation aid according to the cross section from FIG. 7, also with a "C"-shaped design.

FIG. 9 is a cross section of an additional stirrer installation aid with a "U"-shaped design.

DETAILED DESCRIPTION OF THE PREFERRED EMBODIMENTS

Figure 1:
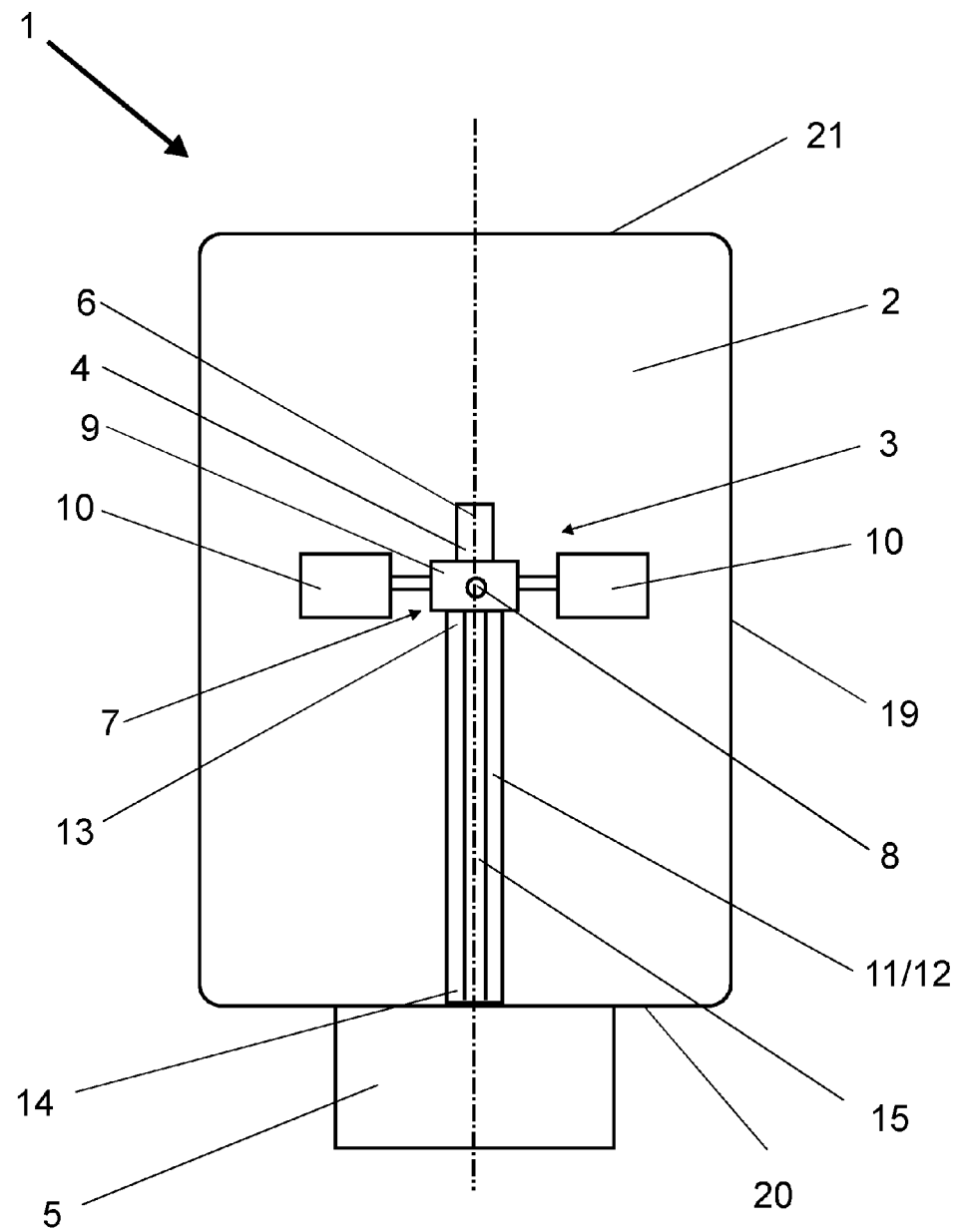
FIG. 1 is a lateral, partially sectional, view of a bioreactor with a stirrer having a stirrer element, the position of the latter on the stirrer shaft being determined by an installation sleeve.

A bioreactor 1 basically consists of a reactor interior 2 with a stirrer 3.

The stirrer 3 consists of a stirrer shaft 4 extending into the reactor interior 2, the stirrer shaft 4 being driveable by a drive 5, e.g. a motor, and having a stirrer element 7 positioned at its free end 6 facing away from the drive 5. In the exemplary embodiment shown in FIG. 1, the stirrer element is fixed to the stirrer shaft 4 with a screw 8. The stirrer element 7 consists of a ring-shaped connector 9 that can be placed on the free end 6 of the stirrer shaft and radially extending stirrer paddles 10. A stirrer installation aid 11 is placed on the stirrer shaft 4, said stirrer installation aid 11 being designed as a sleeve 12 with a slot 15 extending between its axial ends 13, 14. The slot 15 is delimited by the opposite flanks 16, 17 of the wall 18.

The position of the stirrer element 7 on the stirrer shaft 4 is predetermined by the sleeve 12, which is used as a stirrer installation aid 11 and whose second or upper axial end 13, in the installation shown in FIG. 1, is abutted by the stirrer element 7 and its connector 9. The sleeve 12 is designed to be elastic, i.e. flexible, so that its slot 15 can be expanded to such an extent that it can be both laterally placed onto and laterally removed from the stirrer shaft 4.

The reactor interior 2 is delimited laterally by a reactor wall 19, by a reactor floor 20 in the downward vertical direction, and by a reactor ceiling 21 in the upward vertical direction.

In order to position the stirrer element 7 on the stirrer shaft 4 (see FIG. 2), in a step a) the stirrer installation aid 11/sleeve 12 is placed on the stirrer shaft 4, whereby its lower or first axial end 14 abuts on the adjacent reactor floor 20 (see FIG. 3), for example. In a subsequent step b), the stirrer element 7 is placed with its connector 9 on the free end 6 of the stirrer shaft so that its abutment surface 22 abuts on the upper or second axial end 13 of the sleeve 12. In a step c), the stirrer element 7 is fixed to the stirrer shaft 4 by the screw 8 (see FIG. 4). In a subsequent step d), the stirrer installation aid 11/sleeve 12 is then removed from the stirrer shaft 4 by pulling it off laterally.

Figure 11:
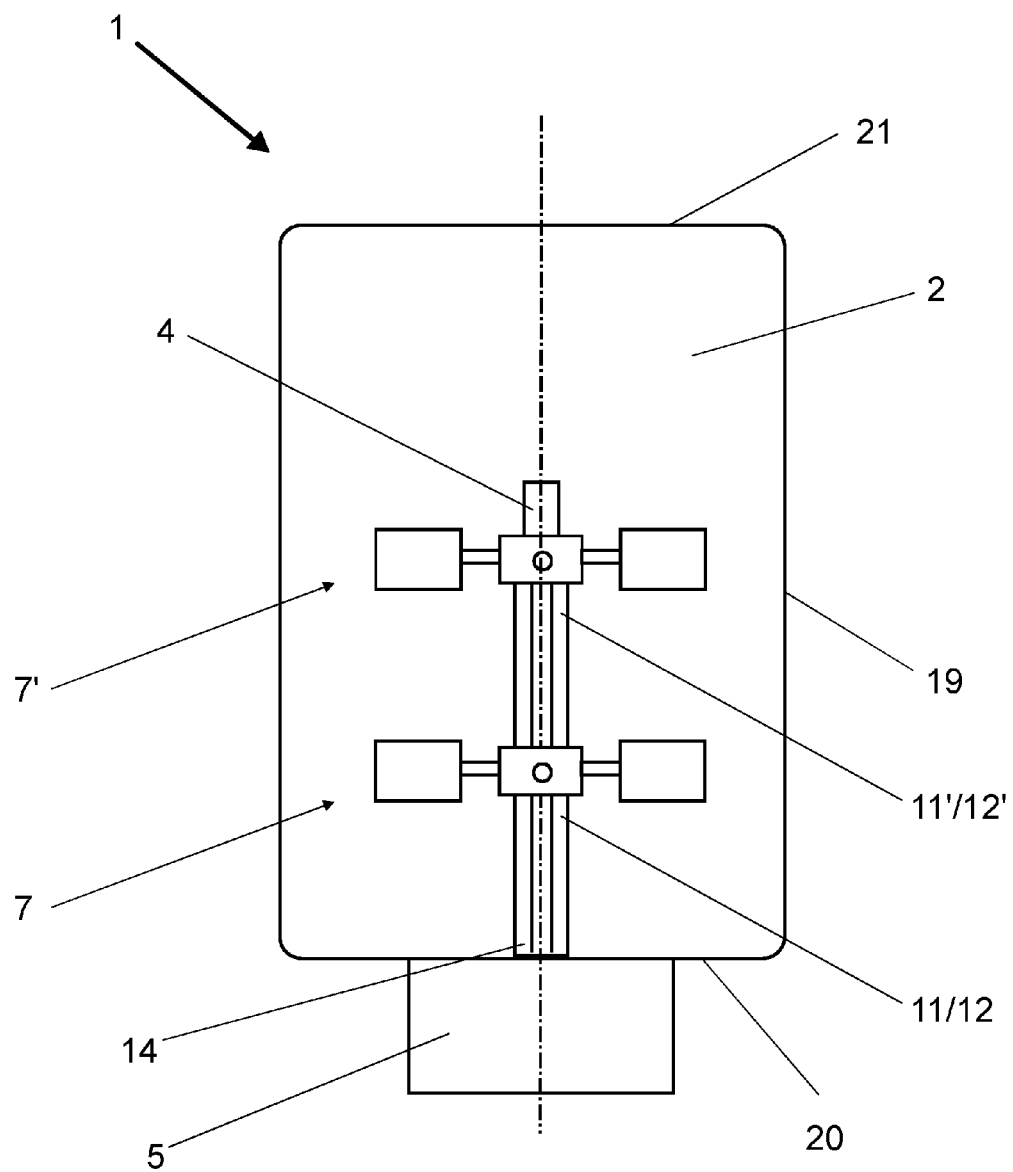
FIG. 11 is a lateral, partially sectional, view of a bioreactor with a stirrer having stirrer elements, the position of the latter on the stirrer shaft being determined by installation sleeves.

To install multiple stirrer elements 7, 7' on the stirrer shaft 4 arranged within the bioreactor 1 (see FIG. 11), at least one further stirrer element 7' is installed on the stirrer shaft 4 arranged within the bioreactor 1 following installation of the first stirrer element 7, with the following steps being carried out:

a') placing a second sleeve 12' which is slotted in the axial longitudinal direction over the entire length of the sleeve, which sleeve also forms a stirrer installation aid 11', on the first stirrer element 7 fixed to the stirrer shaft 4, b') placing a second stirrer element 7' on the free end of the stirrer shaft 4 until it abuts on the adjacent end of the second sleeve 12', c') fixing the second stirrer element 7' on the stirrer shaft 4, d') removing the second sleeve 12'.

If necessary, in a step e), the steps a') to d') are repeated multiple times to fix additional stirrer elements 7, 7' to the stirrer shaft 4.

The cross section of the sleeve 12 can be designed in a "C" shape according to FIGS. 7 and 8. The width of the slot 15, 15' formed by the space between the opposing flanks 16, 17 and 16', 17', respectively, depends in particular on the elasticity of the sleeve material. In principle, however, the cross section of the stirrer installation aid 11 can also be designed in a "U" shape, and the space between the opposing flanks 16", 17" of the slot 15" corresponds approximately to the interior diameter of the sleeve 12.

Figure 10:
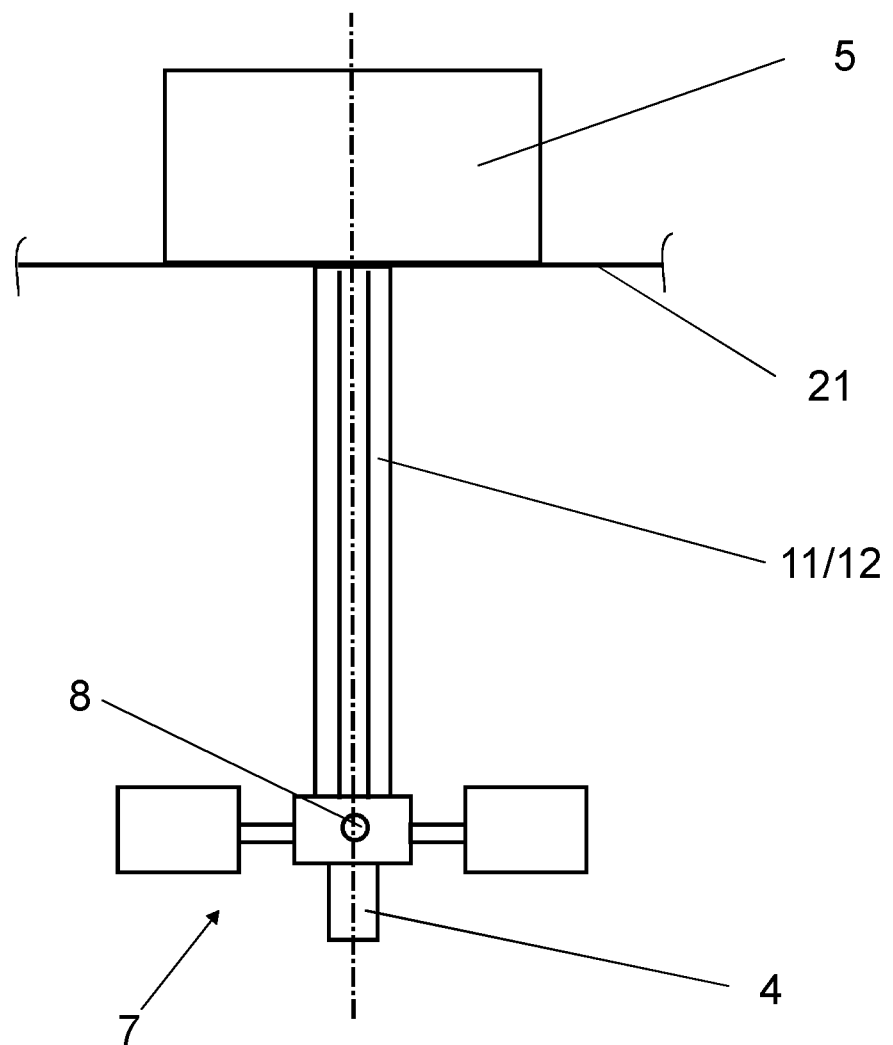
FIG. 10 is a lateral detail view of an additional bioreactor, with a stirrer element, stirrer shaft and stirrer installation aid arranged in suspended configuration.

Although the stirrer element 4 is arranged upright in FIGS. 1 to 9 and 11, it can also be arranged in a suspended configuration, as per FIG. 10.

Of course, the embodiments discussed in the specific description and shown in the figures are merely illustrative exemplary embodiments of the present invention. In light of the present disclosure, a person skilled in the art has a broad spectrum of optional variations available. In particular, the stirrer element 7, the stirrer shaft 4 and the stirrer installation aid 11 can also be arranged in a suspended configuration on the bioreactor 1 or they may be arranged laterally on the reactor wall 19. At a minimum, the stirrer installation aid 11 should be designed so that it at least partially encloses the stirrer shaft 4, can exert a firm clamping action, and can be removed laterally.

LIST OF REFERENCE NUMBERS

1 Bioreactor
2 Reactor interior
3 Stirrer
4 Stirrer shaft of 3

5 Drive
6 Free end of 4
7, 7' Stirrer element
8 Screw
9 Connector of 7
10 Stirrer paddle of 7
11 Stirrer installation aid
12, 12' Sleeve
13 Second axial end of 12
14 First axial end of 12
15, 15', 15" Slot of 12
16, 16', 16" Flank of 12
17, 17', 17" Flank of 12
18, 18', 18" Wall
19 Reactor wall of 1
20 Reactor floor of 1
21 Reactor ceiling of 1
22 Abutment surface of 9

The invention claimed is:

1. A bioreactor comprising:
a stirrer shaft (4) that is driveable by a drive (5);
a stirrer element (7) positioned on the stirrer shaft (4); and
a stirrer installation aid (11) defining a sleeve (12) having opposite inner and outer surfaces and opposite first and second axial ends (14, 13), the sleeve (12) being mounted on the stirrer shaft (7) so that the inner surface faces and extends partly around the stirrer shaft (4), the second axial end defining an abutment surface (22) on which the stirrer element (7) abuts, the stirrer installation aid (11) having a slot (15, 15', 15") extending from the inner surface to the outer surface and from the first axial end to the second axial end (13, 14) of the sleeve, the slot (15, 15' 15") being delimited by opposite flanks (16, 16', 16", 17, 17', 17") of a wall (18, 18', 18") that forms the sleeve (12), and the opposite flanks (16, 16', 16", 17, 17', 17") of the slot (15, 15', 15") being spaced from one another to define a slot width that enables the stirrer installation aid (11) to be pulled off laterally from the stirrer shaft (4).

2. The bioreactor of claim 1, wherein
the stirrer installation aid (11) is placed on the stirrer shaft (4) so that a first axial end (14) of the stirrer installation aid (11) abuts on a mounting surface of the bioreactor (1),
and
the slot (15, 15', 15") being dimensioned to permit the stirrer installation aid (11) to be removed laterally after the stirrer element (7) has been fastened to the stirrer shaft (4).

3. The bioreactor of claim 2,
wherein
the stirrer installation aid (11) is made of an elastic material and is expandable to widen the slot (15, 15', 15").

4. The bioreactor of claim 3,
wherein
the stirrer installation aid (11) has a "C"-shaped cross section.

5. The bioreactor of claim 3,
wherein
the stirrer installation aid (11) has a "U"-shaped cross section.

6. The bioreactor of claim 2,
wherein
the sleeve has a length determined by a spacing of the axial ends (13, 14) and determines a position of the stirrer element (7) on the stirrer shaft (4).

* * * * *